United States Patent [19]
Mesquitta

[11] Patent Number: 5,827,510
[45] Date of Patent: Oct. 27, 1998

[54] HAIR GROWTH PREPARATION

[76] Inventor: Trevor E. Mesquitta, 69 N. Beacon St., Hartford, Conn. 06105

[21] Appl. No.: 939,672

[22] Filed: Sep. 29, 1997

[51] Int. Cl.$^6$ .................. A61K 7/07; A61K 7/00
[52] U.S. Cl. .................. 424/74; 424/195.1; 514/880
[58] Field of Search .................. 424/74, 195.1; 514/880

[56] References Cited

U.S. PATENT DOCUMENTS

| | | | |
|---|---|---|---|
| 75,806 | 3/1868 | Stearns | 424/74 |
| 87,618 | 3/1869 | Baker | 424/74 |
| 99,487 | 2/1870 | Smith | 424/74 |
| 123,270 | 2/1872 | Stock et al. | 424/74 |
| 4,511,555 | 4/1985 | Faust | 424/74 |
| 4,861,593 | 8/1989 | Spearmon et al. | 424/195.1 |
| 5,116,607 | 5/1992 | Jones | 424/70 |
| 5,215,760 | 6/1993 | Kavoussi et al. | 424/680 |
| 5,695,748 | 12/1997 | Francis | 424/74 |

FOREIGN PATENT DOCUMENTS

| | | | |
|---|---|---|---|
| 361097211 | 5/1986 | Japan | 424/74 |
| 402276561 | 11/1990 | Japan | 424/74 |

*Primary Examiner*—Sally Gardner-Lane
*Attorney, Agent, or Firm*—Alix, Yale & Ristas, LLP

[57] ABSTRACT

Hair care preparation which promotes the growth of new hair, helps prevent dry, thinning hair and minimizes hair breakage and split ends. The preparation contains a combination of 10% to 40% of water, 1% to 10% of castor oil, and 50% to 90% of glycerin. These compositions are characterized by the fact that the glycerin acts as a hair penetrant, a carrier for the castor oil and the water, and provides shine and lubricates the hair sheath, the water moisturizes the hair sheath, and the castor oil nourishes and softens the hair.

4 Claims, No Drawings

HAIR GROWTH PREPARATION

BACKGROUND OF THE INVENTION

This invention relates generally to cosmetic preparations for the hair. More particularly, the present invention relates to cosmetic preparations for the hair that promote hair growth.

Human hair is treated in many different ways with various preparations, including, for example shampoos, tinting preparations, dyeing preparations, bleaching preparations, straightening preparations and curling preparations. Each one of these treatments can cause damage to the hair resulting in poor hair growth or hair loss. Various cosmetic preparations are known for repairing damaged hair, including hot oil treatments to replace the oils removed by shampoo and many other hair conditioners that are designed to repair the damage caused by the hair treatments listed above.

However, such cosmetic preparations are unsatisfactory in many ways. Many of the treatments contain chemical compounds that are not needed to repair the hair. Such unneeded chemical compounds may cause additional damage to the hair or coat the hair in a manner that adversely impacts the appearance of the hair. Other treatments target specific types of damage and may require combination with other cosmetic treatments to repair all of the damage to the hair. Interactions between the various cosmetic treatments may create additional difficulties. Persons having sensitive skin may experience adverse reactions to the chemicals present within these cosmetic treatments.

Further, most of the conventional cosmetic treatments are designed for use with hair from persons of Caucasian descent. Although such cosmetic treatments may provide some benefit to the hair of persons of African descent, the differences in the structure of these person's hair limits the efficacy of these treatments. In addition many of the conventional cosmetic treatments are greasy in nature and clog the pores of the scalp, further aggravating the problem that they intended to correct.

SUMMARY OF THE INVENTION

Briefly stated, the invention in a preferred form is a hair growth preparation, and associated method, which contains a combination of active substances consisting essentially of water, castor oil and glycerin. The preparation may contain a range of concentrations of these active substances. The water may comprise 10% to 40% of the preparation by weight, the castor oil may comprise 1% to 10% of the preparation by weight, and the glycerin may comprise 50% to 90% of the preparation by weight. Preferably, the preparation comprises 15% to 20% water, 4% to 6% castor oil, and 70% to 80% glycerin. More preferably, the preparation consists of about 18% water, about 5% castor oil, and about 77% glycerin, by weight.

It is an object of the invention to provide a new and improved hair growth preparation and method that promotes hair growth, prevents dry, thinning hair and minimizes hair breakage and split ends. This object is realized by the use of the active substances listed above. The glycerin acts as a carrier for the castor oil and the water such that the all of the elements of the preparation penetrate the hair sheath. The water moisturizes the hair sheath, the unsaturated fatty acids present in the castor oil nourish and soften the hair, and the glycerin provides shine and lubricates the hair sheath, in addition to acting as a penetrant and carrier.

Other objects and advantages of the invention will become apparent from the specification.

DETAILED DESCRIPTION OF THE INVENTION

A hair growth preparation in accordance with the invention comprises three main ingredients: water; castor oil (ricinus oil) and glycerin (glycerol). The composition is prepared by mixing together the water and emulsified castor oil in a glycerin base.

Glycerin is a simple trihedric alcohol having the form of $CH_2OHCHOHCH_2OH$. The glycerin has penetrative properties that allow it to penetrate the hair's protective sheath. The glycerin also acts as a carrier for the castor oil and the water such that the all of the elements of the preparation penetrate the hair sheath. The water moisturizes the sheath to replace moisture that is removed by other hair treatments and during drying of the hair. Castor oil is pale yellow, viscous oil obtained by cold pressing the seeds of Ricinus communis. The fatty acid composition is approximately: ricinoleic-87%; oleic-7%; linoleic-3%; palmitic-2%; stearic-1%; and trace amounts of dihydroxystearic. The unsaturated fatty acids present in the castor oil nourish and soften the hair with its emollient and moisture binding properties. In addition to acting as a penetrant and a carrier, the glycerin provides shine and lubricates the hair sheath.

More importantly, the penetrating property of the glycerin allows the preparation to be applied directly to the hair follicle to promote the growth of healthy hair. Many people of African descent experience problems with hair growth, which can be attributed to the lack of moisture and fatty acids at the cellular level of the hair follicle. The addition of the castor oil's unsaturated fatty acids to the hair follicle cells aids in the promotion of hair growth by greatly reducing the occurrence of dry, thinning hair, hair breakage and split ends. The addition of the water to the hair follicle cells optimize the water content of the cells. The glycerin also helps the hair follicle cells retain the water and fatty acids that are added by the preparation.

Small amounts of biotin, riboflavin, carrot seed oil and hemp seed oil may be added to the main ingredients of the hair growth preparation. For example 0% to 10% of biotin, 0% to 15% of riboflavin, 0% to 15% of hemp seed oil, and 0% to 5% of carrot seed oil may be added to further promote the growth of hair. The biotin reduces the incidence of split end and promotes hair growth. The riboflavin promotes hair growth. The carrot seed oil is rich in beta carotene and vitamins A and E. The vitamin A improves the sheen of the hair and reduces the incidence of dry, thinning hair. The vitamin E also helps improve the sheen of the hair and improves the oxygen intake to the cells of the hair follicle. The hemp seed oil is rich in essential fatty acids and protein and helps maintain the structure of the hair.

The preparation also is beneficial for the skin, providing improved moisturization, skin elasticity, and oxygen intake, thereby promoting cell growth, healing and regeneration. African shea butter may also be added to provide additional care for the scalp and other skin. For example 0% to 10% of African shea butter may be added to nourish the skin and to relieve the ashiness to which dark skin is subject.

Table 1 provides the active substances, and the proportions of these active substances that comprise the preparation.

TABLE 1

| Ingredient | Allowable Range (% by weight) | Preferred Composition (% by weight) | Most Preferred Composition (% by weight) |
|---|---|---|---|
| Water | 10% to 40% | 15% to 20% | 18% |
| Castor Oil | 1% to 10% | 4% to 6% | 5% |
| Glycerin | 50% to 90% | 70% to 80% | 77% |
| Biotin | 0% to 10% | 2% to 8% | 4% to 6% |
| Riboflavin | 0% to 15% | 5% to 10% | 7% to 8% |
| Hemp Seed Oil | 0% to 15% | 5% to 10% | 7% to 8% |
| Carrot Seed Oil | 0% to 5% | 2% to 3% | 2% to 3% |

EXAMPLE

The preparation has been tested on adults, children and babies. Preferably bi-weekly applications of the preparation have been found to promote the growth of hair in areas of the scalp that had exhibited difficulty in growing hair. Hair and scalp treated with the invention remained moist for the full period of time between the bi-weekly applications and dry/flaky scalp was eliminated. Application of the preparation on men has also demonstrated that the preparation may be used to promote growth of facial hair, such as beards, and to improve the quality of such facial hair. Application of the preparation to children and babies did not result in any adverse reactions.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. Preparation for treating hair consisting of:
   18% by weight of water;
   5% by weight of castor oil; and
   77% by weight of glycerin.

2. Preparation for treating hair comprising:
   about 15% to 20% by weight of water;
   about 4% to 6% by weight of castor oil;
   about 70% to 80% by weight of glycerin;
   about 2% to 8% by weight of biotin;
   about 5% to 10% by weight of riboflavin;
   about 5% to 10% by weight of hemp seed oil; and
   about 2% to 3% by weight of carrot seed oil.

3. Method of treating hair comprising the step of periodically applying a preparation comprising:
   about 15% to 20% by weight of water;
   about 4% to 6% by weight of castor oil;
   about 70% to 80% by weight of glycerin;
   about 2% to 8% by weight of biotin;
   about 5% to 10% by weight of riboflavin;
   about 5% to 10% by weight of hemp seed oil; and
   about 2% to 3% by weight of carrot seed oil.

4. The method of claim 3 wherein the preparation is applied every two weeks.

* * * * *